(12) United States Patent
Imamura et al.

(10) Patent No.: US 11,291,993 B2
(45) Date of Patent: Apr. 5, 2022

(54) MICRO-FLUID CHIP (71) Applicant: SEKISUI CHEMICAL CO., LTD., Osaka (JP)

(72) Inventors: Kazuhiko Imamura, Osaka (JP); Nobuhiko Inui, Osaka (JP); Shotaro Kobaru, Osaka (JP); Takamasa Kouno, Osaka (JP); Tatsunori Takamatsu, Tokyo (JP); Ryoma Ishii, Osaka (JP); Ryosuke Takahashi, Osaka (JP); Tsutomu Nakamura, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 46 days.

(21) Appl. No.: 16/759,974

(22) PCT Filed: Nov. 21, 2018

(86) PCT No.: PCT/JP2018/042916
§ 371 (c)(1),
(2) Date: Apr. 28, 2020

(87) PCT Pub. No.: WO2019/107231
PCT Pub. Date: Jun. 6, 2019

(65) Prior Publication Data
US 2020/0276581 A1 Sep. 3, 2020

(30) Foreign Application Priority Data
Nov. 29, 2017 (JP) .............................. JP2017-229079

(51) Int. Cl.
*B01L 3/00* (2006.01)
(52) U.S. Cl.
CPC ... *B01L 3/502715* (2013.01); *B01L 2300/041* (2013.01); *B01L 2300/0819* (2013.01)

(58) Field of Classification Search
CPC .. B01L 3/502715; B01L 3/5027; B01L 3/502; B01L 3/50; B01L 2300/041;
(Continued)

(56) References Cited

U.S. PATENT DOCUMENTS

2002/0192701 A1 12/2002 Adey
2004/0037739 A1 2/2004 McNeely et al.
(Continued)

FOREIGN PATENT DOCUMENTS

EP 1 977 830 A1 10/2008
JP 2005-513441 A 5/2005
(Continued)

OTHER PUBLICATIONS

English Machine Translation for JP 2009-284769 A, Takeda, obtained from U.S. Appl. No. 16/617,315 on Aug. 9, 2021, pp. 1-23. (Year: 2021).*
(Continued)

*Primary Examiner* — Christine T Mui
(74) *Attorney, Agent, or Firm* — Cheng Law Group, PLLC (57) ABSTRACT

Provided is a micro-fluid chip that enables reducing contamination between branch channels, has a relatively simple channel structure and facilitates miniaturization. A micro-fluid chip (1) having a channel structure (3) through which a fluid is delivered, wherein the channel structure (3) includes: a main channel (4) having an inflow port (5) and an outflow port (6); a plurality of branch channels (11) to (13) connected to the main channel (4), each branch channel having an inflow end on a side connected to the main channel (4) and an outflow end that is an end portion on an opposite side to the inflow end; and a sub-branch channel (14) connected to the main channel (4) between at least one pair of adjacent branch channels (11) and (12) among the
(Continued)

plurality of branch channels (11) to (13), the sub-branch channel (14) having an inflow end on a side connected to the main channel (4).

7 Claims, 12 Drawing Sheets (58) Field of Classification Search
CPC ......... B01L 2300/04; B01L 2300/0891; B01L 2300/0809; B01L 2300/08
USPC .......................................... 422/502, 500, 50
See application file for complete search history.

(56) References Cited

U.S. PATENT DOCUMENTS

| | | |
|---|---|---|
| 2004/0109793 A1 | 6/2004 | McNeely et al. |
| 2005/0019898 A1 | 1/2005 | Adey et al. |
| 2006/0094004 A1 | 5/2006 | Nakajima et al. |
| 2008/0254468 A1 | 10/2008 | Glauser |
| 2010/0105866 A1 | 4/2010 | Fraden et al. |
| 2011/0036862 A1* | 2/2011 | Kanai ............... B01L 3/502723 422/509 |

FOREIGN PATENT DOCUMENTS

| | | | |
|---|---|---|---|
| JP | 2006-217818 A | 8/2006 | |
| JP | 2008-253261 A | 10/2008 | |
| JP | 2009-284769 | * 12/2009 | .............. C12M 1/00 |
| WO | WO-2006116616 A2 | 11/2006 | |
| WO | WO-2017/075295 A1 | 5/2017 | |

OTHER PUBLICATIONS

International Search Report for the Application No. PCT/JP2018/042916 dated Feb. 19, 2019.
Written Opinion of the International Searching Authority (PCT/ISA/237) for Application No. PCT/JP2018/042916 dated Feb. 19, 2019.
Written Opinion of the International Searching Authority (PCT/ISA/237) for Application No. PCT/JP2018/042916 dated Feb. 19, 2019 (English Translation dated Jun. 11, 2020).
Supplementary European Search Report for the Application No. EP 18 883 728.0 dated Jul. 21, 2021.

* cited by examiner

MICRO-FLUID CHIP

TECHNICAL FIELD

The present invention relates to a micro-fluid chip having a channel structure through which a fluid is delivered.

BACKGROUND ART

Conventionally, various micro-fluid chips have been known. For example, in a micro reactor for genetic testing described in Patent Literature 1 below, a plurality of reaction chambers are provided for a plurality of branch channels branched from a main channel, respectively. Here, in order to prevent contamination, a reagent delivering component and a control/detection component are independently formed for each specimen. With the use of check valves on the upstream side and the downstream side of each reaction chamber, contamination between the reaction chambers is prevented.

Patent Literature 2 below discloses the use of a gas generation valve in order to prevent movement of fluid.

CITATION LIST

Patent Literature

Patent Literature 1: Japanese Patent Laid-Open No. 2006-217818
Patent Literature 2: Japanese Patent Laid-Open No. 2008-253261

SUMMARY OF INVENTION

Technical Problem

As described in Patent Literature 1 and Patent Literature 2, in a micro-fluid chip having a plurality of reaction chambers, a check valve or a gas generator valve has to be used for each reaction chamber in order to prevent contamination between the reaction chambers. Hence, there have been problems such as an increase in the number of valves for controlling such liquid delivery, and complicated structure. It has also been difficult to miniaturize micro-fluid chips.

It is an object of the present invention to provide a micro-fluid chip capable of reducing the number of valves for fluid delivery control, simplifying the channel structure, and effectively achieving further miniaturization.

Solution to Problem

A micro-fluid chip according to the present invention is a micro-fluid chip having a channel structure through which a fluid is delivered, wherein the channel structure includes: a main channel having an inflow port through which the fluid enters and an outflow port through which the fluid flows out; a plurality of branch channels connected to the main channel, each of the branch channels having an inflow end on a side connected to the main channel and an outflow end that is an end portion on an opposite side to the inflow end; and a sub-branch channel connected to the main channel between at least one pair of adjacent branch channels among the plurality of branch channels, the sub-branch channel having an inflow end on a side connected to the main channel. In the micro-fluid chip according to the present invention, preferably, the sub-branch channel has no outflow end.

In the micro-fluid chip according to the present invention, preferably, the inflow end of the sub-branch channel is open to an inner wall surface of the main channel shared by the inflow ends of two or more of the branch channels. In this case, contamination between the branch channels can be more effectively prevented.

In another specific aspect of the micro-fluid chip according to the present invention, an inner wall where the branch channels and the sub-branch channel are open is an inner wall positioned in a direction orthogonal to a direction in which the branch channels extend. In a further specific aspect of the micro-fluid chip according to the present invention, a transverse cross section of the main channel is rectangular.

In other specific aspect of the micro-fluid chip according to the present invention, the sub-branch channel is provided at all positions between adjacent branch channels. In this case, it is possible to more effectively prevent contamination between all of adjacent branch channels.

In still another specific aspect of the micro-fluid chip according to the present invention, the sub-branch channel has a portion with a channel cross-sectional area larger than a channel cross-sectional area at the inflow end of the sub-branch channel connected to the main channel. In this case, the fluid can be reliably guided into the sub-branch channel. The fluid guided into the sub-branch channel is unlikely to leak out of the sub-branch channel. Therefore, contamination can be more reliably prevented.

In yet another specific aspect of the micro-fluid chip according to the present invention, the micro-fluid chip further includes a connection channel connected to the outflow end side of the plurality of branch channels, wherein the connection channel is connected to the main channel.

In other specific aspect of the micro-fluid chip according to the present invention, the inflow end and the outflow end of the main channel are provided with a seal part capable of stopping the fluid from moving.

Advantageous Effects of Invention

In the micro-fluid chip according to the present invention, since a valve or the like for fluid delivery control does not need to be provided for each of the branch channels, it is possible to reduce the number of valves or the like and simplify the channel structure. In addition, it is also possible to facilitate miniaturization of the micro-fluid chip.

DESCRIPTION OF EMBODIMENTS

Hereinafter, the present invention will be clarified by describing specific embodiments of the present invention with reference to the drawings.

Figure 1:
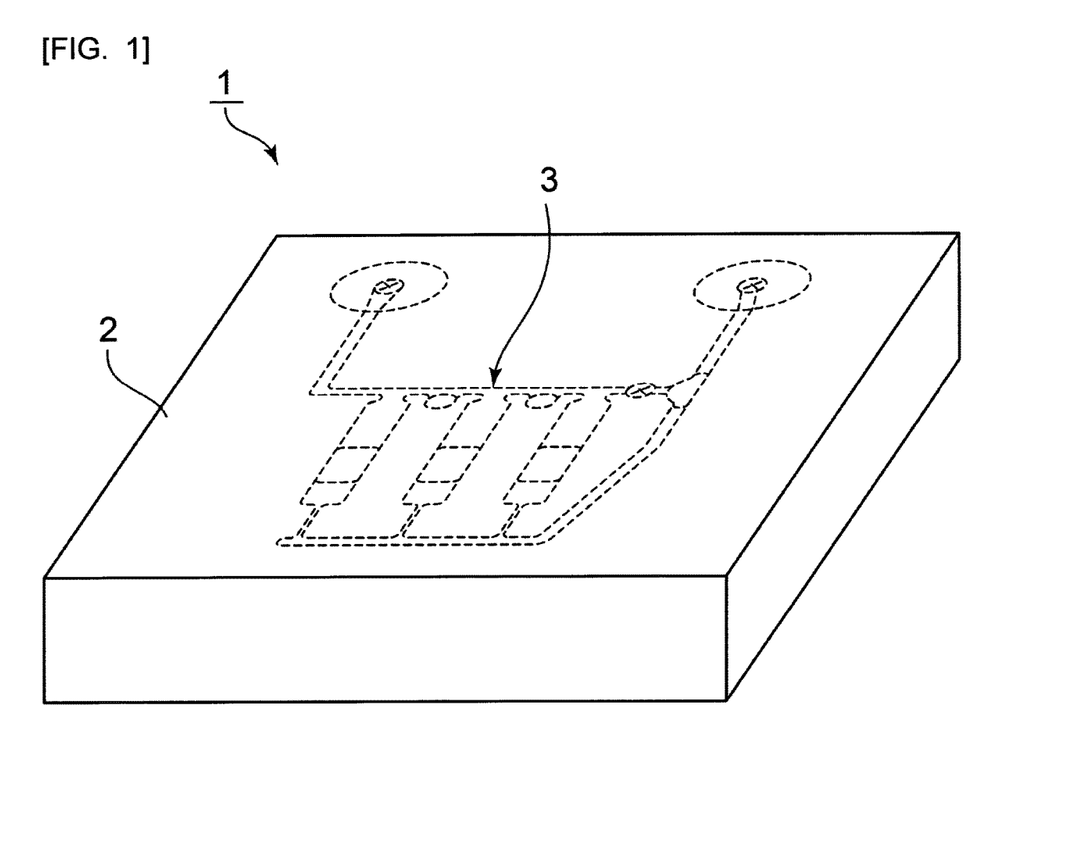
FIG. 1 is a perspective view showing a micro-fluid chip of a first embodiment of the present invention.
Figure 2:
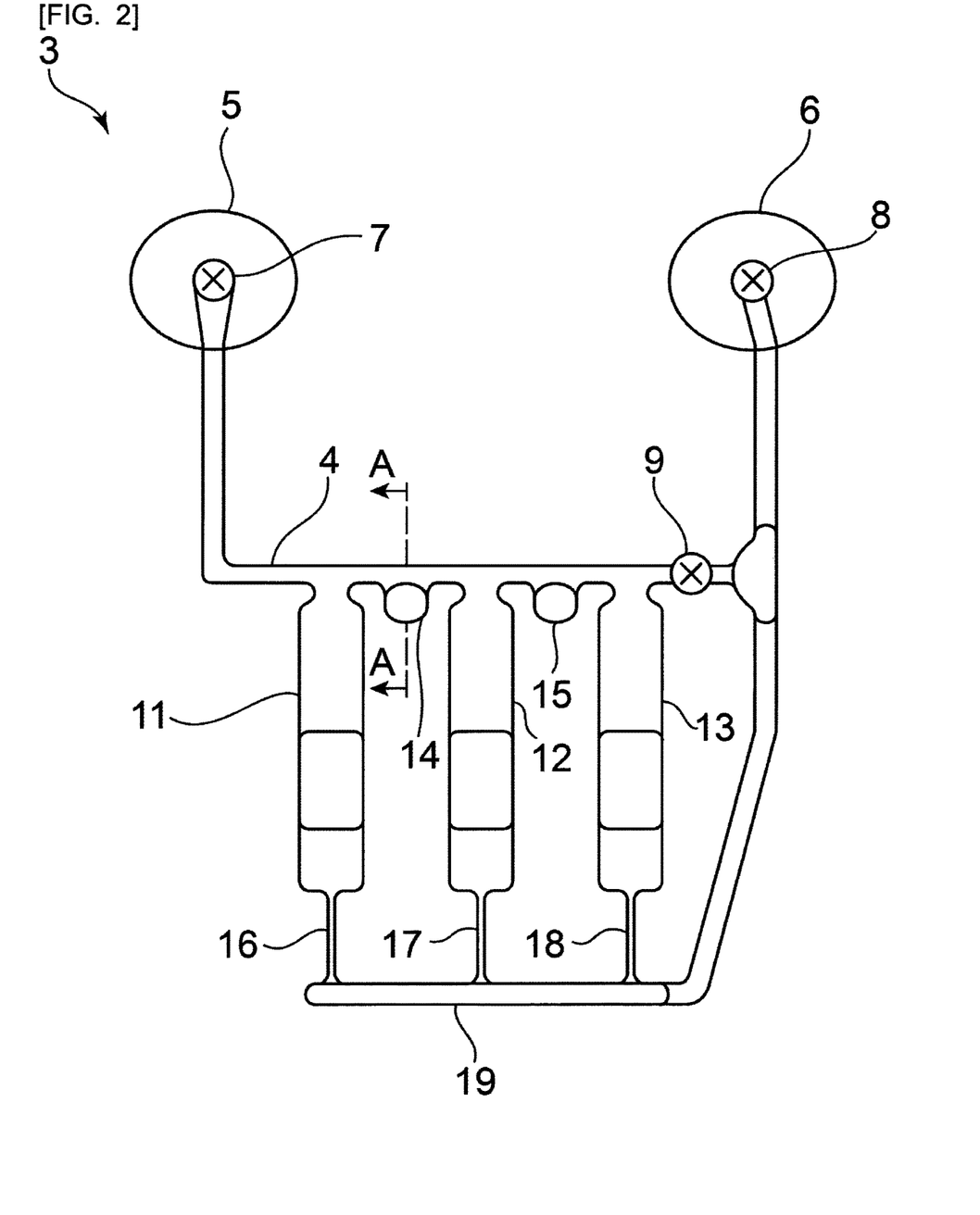
FIG. 2 is a schematic plan view for explaining a channel structure of the micro-fluid chip of the first embodiment of the present invention.

FIG. 1 is a schematic view showing a micro-fluid chip according to the first embodiment of the present invention, and FIG. 2 is a schematic plan view showing the channel structure.

A micro-fluid chip 1 has a chip main body 2 in the form of rectangular plate. The chip main body 2 is composed of a laminate formed by superimposing a plurality of layers one upon another. Material that forms the plurality of layers is made of appropriate material such as synthetic resin and glass.

A channel structure 3 indicated by the broken line in FIG. 1 is provided in the chip main body 2. As shown in FIG. 2, the channel structure 3 is a portion through which a fluid is transported, and the channel structure 3 has a main channel 4. An inflow port 5 is provided at one end of the main channel 4, and an outflow port 6 is provided at the other end. A valve 7 is provided on the inflow port 5 side, and a valve 8 is provided on the outflow port 6 side.

A valve 9 is provided for the main channel 4 on a downstream side relative to a portion where a later-described branch channel 13 is connected. That is, the valve 9 is provided between the portion where the branch channel 13 is connected and the portion where the valve 8 is provided.

The valves 7, 8 and 9 constitute a seal part that can seal the main channel 4. However, instead of the valves 7, 8, 9, it may also be possible to use other seal member that can open and close the main channel 4 by external manipulation.

One end of each of a plurality of branch channels 11 to 13 is connected to the main channel 4. The branch channels 11 to 13 are provided as reaction chambers for PCR reaction. At end portions of the branch channels 11 to 13 on an opposite side to the side connected to the main channel 4, channel resistance portions 16 to 18 having a smaller cross-sectional area than the branch channels 11 to 13 are provided. One end of each of the branch channels 11 to 13 is an inflow end and is open to the main channel 4. The other ends of the branch channels 11 to 13 are outflow ends and are connected to the channel resistance portions 16 to 18.

Downstream ends of the channel resistance portions 16 to 18 are connected to a connection channel 19. The connection channel 19 is connected to the main channel 4 on the downstream side relative to the valve 9.

Between adjacent branch channels 11 and 12, a sub-branch channel 14 is connected to the main channel 4. Also, between adjacent branch channels 12 and 13, a sub-branch channel 15 is connected to the main channel 4. Each of the sub-branch channels 14,15 has an inflow end connected to the main channel 4, but the sub-branch channels 14,15 have no gas outflow port. The inflow ends of the sub-branch channels 14,15 are open to the main channel 4.

The sub-branch channel 14 is provided to prevent specimen and reagent contamination between the branch channels 11 and 12. The sub-branch channel 15 is also provided to prevent contamination between adjacent branch channels 12 and 13.

Figure 3:
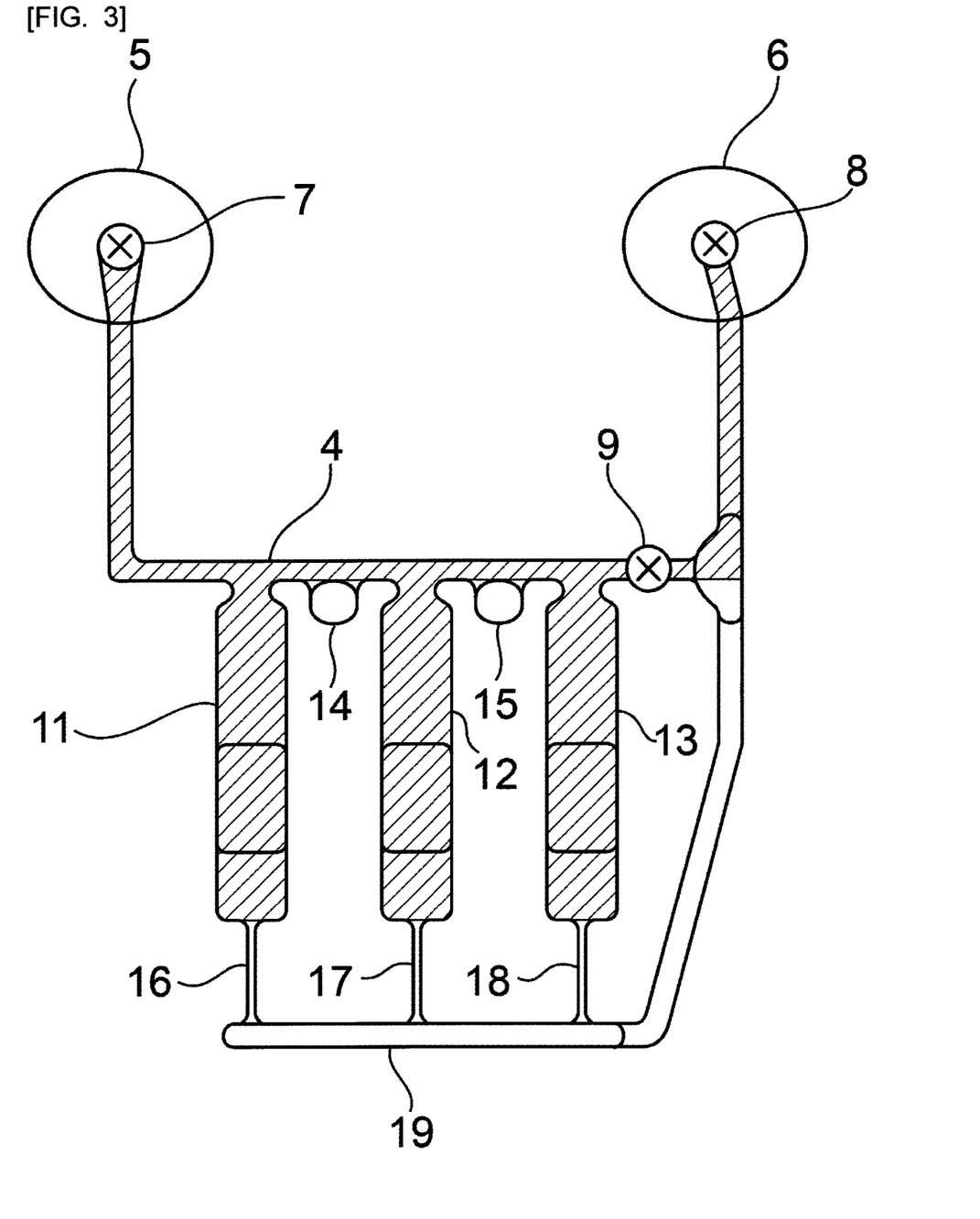
FIG. 3 is a schematic plan view showing a state in which a plurality of branch channels are filled with fluid in the channel structure of the micro-fluid chip according to the first embodiment of the present invention.

In the micro-fluid chip 1, a fluid that is a liquid specimen or liquid reagent is delivered. More specifically, the valves 7, 8, 9 are opened, and the fluid is delivered to the main channel 4 from the inflow port 5. As shown in FIG. 3, the delivered fluid fills the inside of the branch channels 11, 12, 13. In this case, the delivery of fluid is performed at a delivery pressure lower than the channel resistance of the channel resistance portions 16 to 18. Therefore, the fluid is not delivered to the channel resistance portions 16 to 18.

Further, a gas is introduced from the inflow port 5 side to cause the fluid in the main channel 4 to flow out from the outflow port 6. Next, the valves 7 and 9 are closed. In this state, the fluid is not present in the main channel 4. Only the inside of the branch channels 11 to 13 is filled with the fluid.

When the valve 9 is closed, the valve 8 may also be closed.

As described above, the fluid is sealed in the branch channels 11, 12 and 13.

In a PCR reaction, a step of heating a fluid in which RNA or the like is mixed with a reagent, to a predetermined temperature, is repeated. Thus, RNA or the like is subjected to polymerization, and an extended nucleic acid chain is detected using optical detection means or the like. In this case, the fluid as a reaction liquid is repeatedly heated in the branch channels 11, 12, 13 as described above. When the fluid is heated, the fluid expands and tries to move from the branch channels 11 to 13 side to the main channel 4 side. Hence, there is a risk of contamination between the fluid in the branch channel 11 and the fluid in the branch channel 12.

However, in the micro-fluid chip 1, the sub-branch channel 14 is provided between adjacent branch channels 11 and 12. Therefore, even if there is the fluid that has expanded with heat and moved to the main channel 4 side, the fluid enters the sub-branch channel 14, and does not reach the branch channel 12 and the branch channel 11 on the other side. Thus, contamination between the fluids is unlikely to occur between the adjacent branch channels 11 and 12. Also, since the sub-branch channel 15 is provided between the adjacent branch channels 12 and 13, contamination can be similarly prevented.

Figure 4:
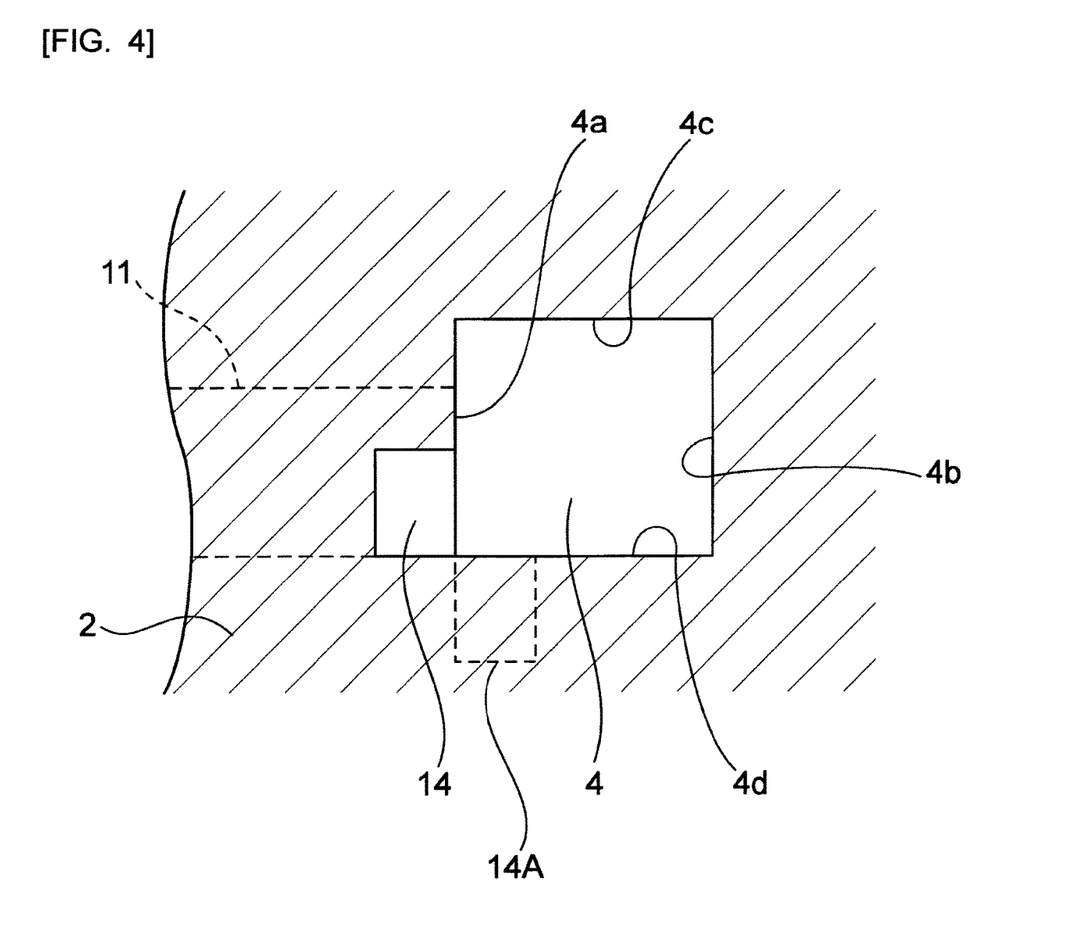
FIG. 4 is a partially cutaway enlarged cross-sectional view for explaining a main channel and a sub-branch channel in the channel structure of the micro-fluid chip of the first embodiment of the present invention.

FIG. 4 is a partially cutaway enlarged cross-sectional view corresponding to a portion along the A-A line in FIG. 2. This section is a transverse cross section of the main channel 4. The main channel 4 has inner wall surfaces 4a to 4d. In the present invention, preferably, the inflow ends of the sub-branch channels 14, 15 are open to the inner wall surface 4a shared by the inflow ends of the plurality of branch channels 11 to 13.

It is desirable that the sub-branch channels 14, 15 be preferably connected to the same inner wall of the main channel 4 to which the branch channels 11 to 13 are connected. Although not particularly limited, the main channel 4 has a rectangular transverse cross-sectional shape in the present embodiment. Therefore, the main channel 4 has four inner walls 4a to 4d. The sub-branch channel 14 is connected to the inner wall 4a among the inner walls. As shown with the broken line, the branch channel 11 is also connected to the inner wall 4a. In the case where the inflow ends of the branch channels 11 to 13 and the inflow ends of the sub-branch channels 14, 15 are open to the same inner wall 4a in this manner, the fluid that has expanded with heat and entered the main channel 4 from the branch channels 11 to 13 can easily enter the sub-branch channel 14 along the inner wall 4a. It is therefore possible to more effectively prevent contamination. However, the inflow ends of the branch channels 11 to 13 and the inflow ends of the sub-branch channels 14, 15 may be open to a different inner wall of the main channel 4. In the present embodiment, the sub-branch channel 14 is extended from the inner wall 4a of the main channel 4 in a direction away from the main channel 4, that is, the direction in which the branch channel 11 and the branch channel 12 extend. However, it may also be possible to use a sub-branch channel 14A shown with the dashed line in FIG. 4. The sub-branch channel 14A is connected to the inner wall 4a and is extended downward from the inner wall 4a of the main channel 4. In this case, the sub-branch channel 14A is also open toward the inner wall surface 4a of the main channel 4 shared by the inflow ends of the plurality of branch channels 11 to 13.

Moreover, like the sub-branch channel 14A, the direction in which the sub-branch channel extends is not limited to the direction in which the branch channels 11 to 13 extend, and may be a depth direction of the main channel 4.

Further, in the present embodiment, the main channel 4 is linearly extended from a portion where the branch channel 11 is connected toward a portion where the branch channel 3 is connected. However, in the present invention, the main channel may have a curved portion between the branch channels. Accordingly, the inflow end of the sub-branch channel may be open in this curved portion.

Although not particularly limited, in the present embodiment, the inner wall 4a of the main channel 4 is positioned in a direction orthogonal to the direction in which the branch channels 11, 12, 13 extend. Thus, it is possible to more effectively prevent contamination between the adjacent branch channels 11 and 12 and between the adjacent branch channels 12 and 13.

In the micro-fluid chip 1, the sub-branch channels 14, 15 are provided between both of a pair of adjacent branch channels 11 and 12 and a pair of branch channels 12 and 13. However, the sub-branch channels are not necessarily provided at all positions between a plurality of pairs of adjacent branch channels. The sub-branch channel needs to be provided between at least one pair of branch channels. It is desirable that the sub-branch channels 14, 15 be preferably provided at all positions between a pair of adjacent branch channels as in the present embodiment.

The sub-branch channels 14, 15 are preferably provided with portions having a larger channel cross-sectional area than the channel cross-sectional area at the inflow ends of the sub-branch channels 14, 15 connected to the main channel 4. Therefore, in the present embodiment, as shown in FIG. 2, a portion with the maximum channel cross-sectional area of the sub-branch channel is provided at a position different from the portion connected to the main channel 4.

Thus, it is desirable that the sub-branch channels 14, 15 be provided with portion(s) having the larger channel cross-sectional area than the channel cross-sectional area of the inflow ends. Consequently, the fluid that has entered due to heat expansion can be more reliably guided into the sub-branch channel 14. In addition, the fluid guided into the sub-branch channel 14 is unlikely to leak out of the sub-branch channel 4.

The portion with the larger channel cross-sectional area of the sub-branch channel can be formed by enlarging at least one of the dimension in the width direction and the dimension in the depth direction of the transverse cross section of the sub-branch channel.

In the micro-fluid chip 1, the cross-sectional shape and size of the channel structure refer to a minute channel that produces micro effects when transporting a fluid. In such a channel structure, the fluid is strongly influenced by surface tension, and behaves differently from the fluid flowing through a regular large size channel.

The transverse cross-sectional shape and size of the channel through which the fluid is delivered are not particularly limited as long as the channel produces the above-described micro effects. Therefore, the transverse cross sections of the main channel 4, the branch channels 11, 12, 13 and the sub-branch channels 14, 15 may be rectangular, circular, ellipse, or the like. For example, in the case where a pump or gravity is used to cause the fluid to flow into the channel through which the fluid is to be delivered, if the transverse cross-sectional shape of the channel is approximately rectangular (including square) from the viewpoint of further reducing the flow resistance, the dimension of the shorter side is preferably not less than 20 μm, more preferably not less than 50 μm, and further preferably not less than 100 μm. Also, from the viewpoint of further miniaturizing the micro-fluid chip 1, the dimension of the shorter side is preferably not more than 5 mm, more preferably not more than 1 mm, and further preferably not more than 500 μm.

If the transverse cross-sectional shape of the channel through which the fluid is delivered is approximately circular, the diameter (the short diameter in the case of an ellipse) is preferably not less than 20 μm, more preferably not less than 50 μm, and further preferably not less than 100 μm. From the viewpoint of further miniaturizing the micro-fluid chip 1, the diameter (the short diameter in the case of an ellipse) is preferably not more than 5 mm, more preferably not more than 1 mm, and further preferably not more than 500 μm.

On the other hand, for example, when a capillary phenomenon is more effectively utilized to cause the fluid to flow into the channel through which the fluid is to be delivered, if the transverse cross-sectional shape of the channel is approximately rectangular (including square), the dimension of the shorter side is preferably not less than 5 μm, more preferably not less than 10 μm, and further preferably not less than 20 μm. Moreover, the dimension of the shorter side is preferably not more than 200 μm, and more preferably not more than 100 μm.

The contamination can be more prevented with an increase in the capacity of the sub-branch channels 14, 15. However, in order to reduce a decrease in the fluid in the sub-branch channels 14, 15 due to condensation, the capacity of the sub-branch channel is desirably not more than 5 μL.

It is desirable that the channel cross-sectional area of the sub-branch channel on the inflow end side be about 0.01 mm$^2$ to 2.0 mm$^2$. In this case, the fluid that has entered the main channel 4 side can be more reliably guided into the sub-branch channels 14, 15.

The distance between a portion of the branch channel 11 which is open in the main channel 4 and a portion of the branch channel 12 which is open in the main channel 4, that is, the distance between the portions which are open in the main channel 4 between the adjacent branch channels 11 and 12 is desirably 10.0 mm or less. In this case, it is possible to miniaturize the micro-fluid chip 1.

However, the distance from the inflow end of each of the branch channels 11, 12 connected to the main channel 4 to the inflow end of the sub-branch channel 14 connected to the main channel 4 is preferably less than 5.0 mm. In this case, the fluid that has entered the main channel 4 due to heat expansion can be reliably guided into the sub-branch channel 14.

The contact angle between the fluid and a wall surface of the channel structure 3 is preferably not less than 20° and not more than 120°. Within this range, the fluid can be reliably guided into the branch channels 11 to 13 as described above to perform the PCR reaction and the like, and contamination can be effectively prevented as described above.

The shapes and arrangement of the main channel and the sub-branch channel in the present invention are not particularly limited. Referring to FIG. 5 to FIG. 10, channel structures in micro-fluid chips of the second to seventh embodiments will be described.

Figure 5:
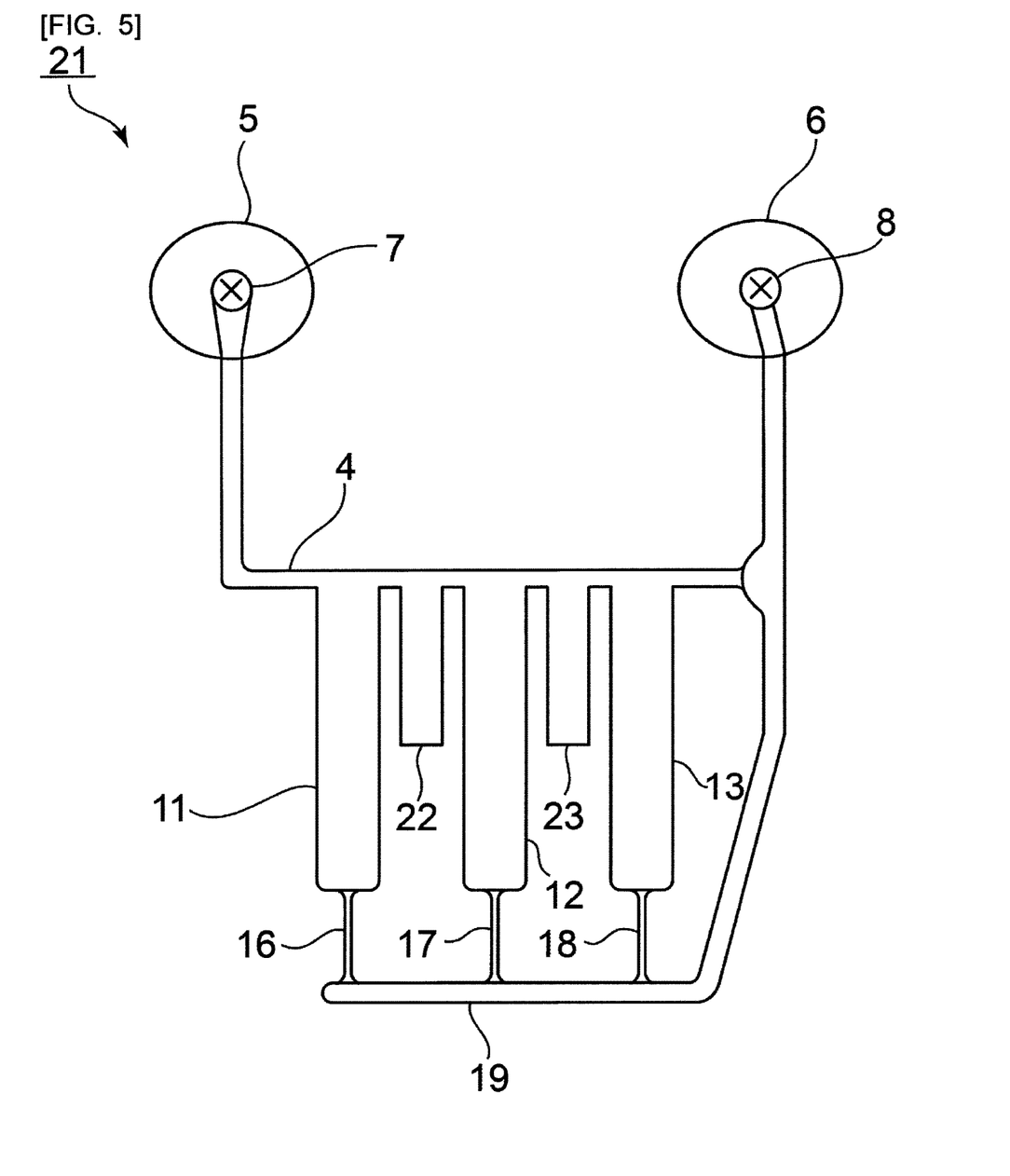
FIG. 5 is a schematic plan view for explaining a channel structure of a micro-fluid chip according to a second embodiment of the present invention.

In the second embodiment shown in FIG. 5, a channel structure 21 is formed in substantially the same manner as the channel structure 3 shown in FIG. 2, except that sub-branch channels 22, 23 which are rectangular in planar shape are used.

Figure 6:
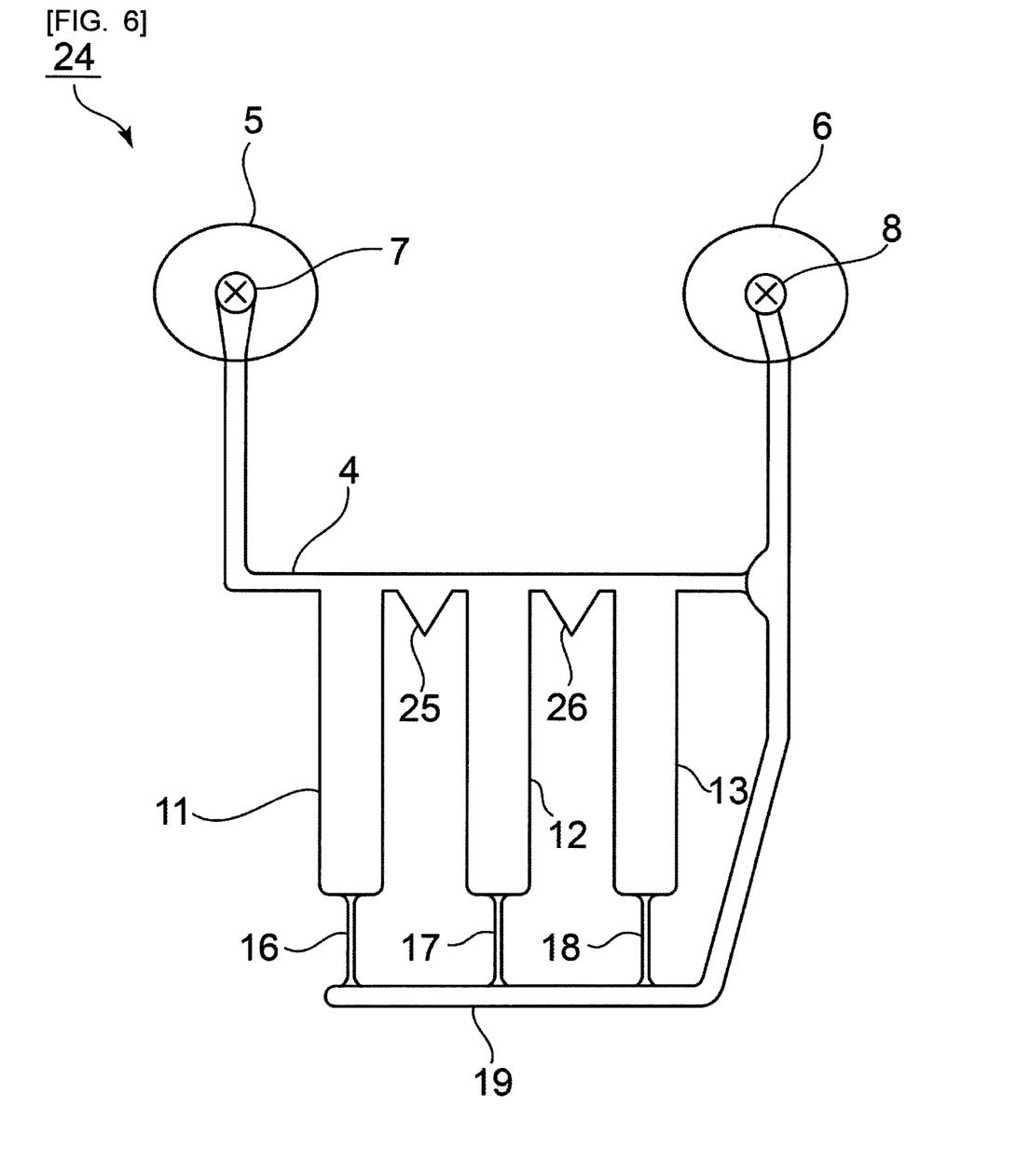
FIG. 6 is a schematic plan view for explaining a channel structure of a micro-fluid chip according to a third embodiment of the present invention.
Figure 7:
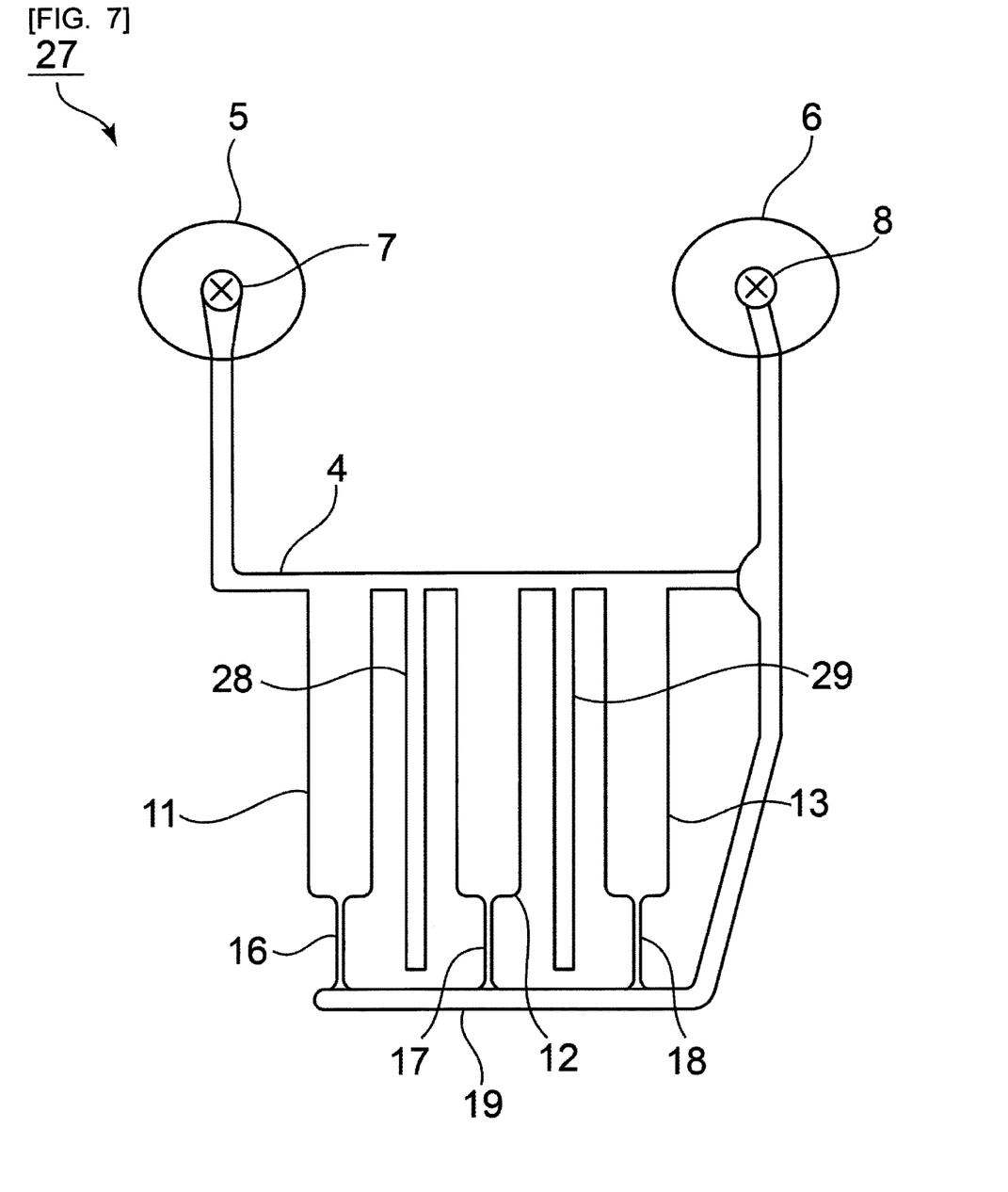
FIG. 7 is a schematic plan view for explaining a channel structure of a micro-fluid chip according to a fourth embodiment of the present invention.

A channel structure 24 in the micro-fluid chip of the third embodiment shown in FIG. 6 is formed in the same manner as the channel structure 3, except that sub-branch channels 25, 26 which are triangular in planar shape are provided. Furthermore, in a channel structure 27 of the micro-fluid chip of the fourth embodiment shown in FIG. 7, sub-branch channels 28, 29 having a rectangular shape longer and thinner than the branch channels 11 to 13 are provided. Thus, as shown in the sub-branch channels 22, 23, 25, 26, 28, 29, the planar shapes of the sub-branch channels are not particularly limited.

Figure 8:
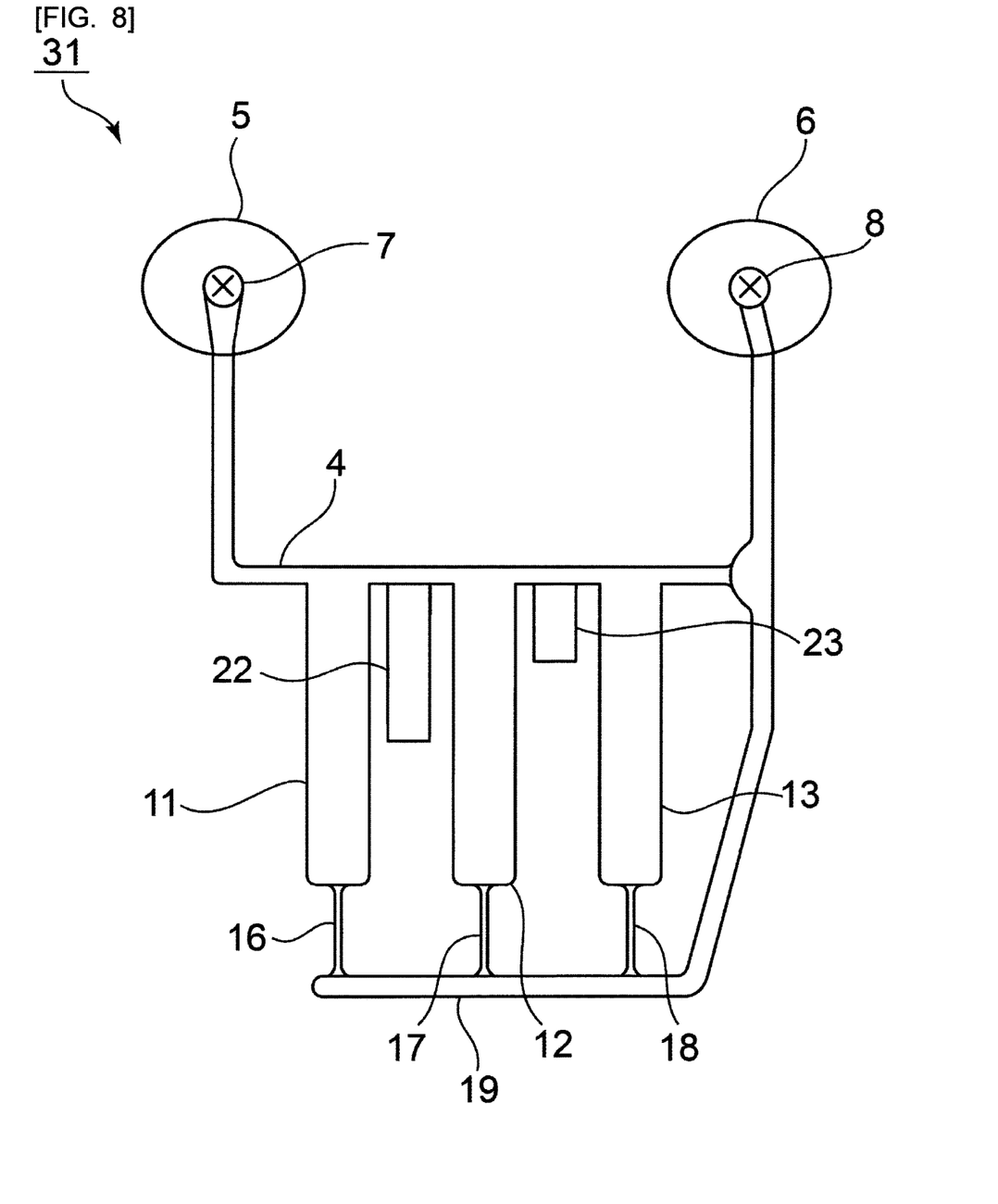
FIG. 8 is a schematic plan view for explaining a channel structure of a micro-fluid chip according to a fifth embodiment of the present invention.
Figure 9:
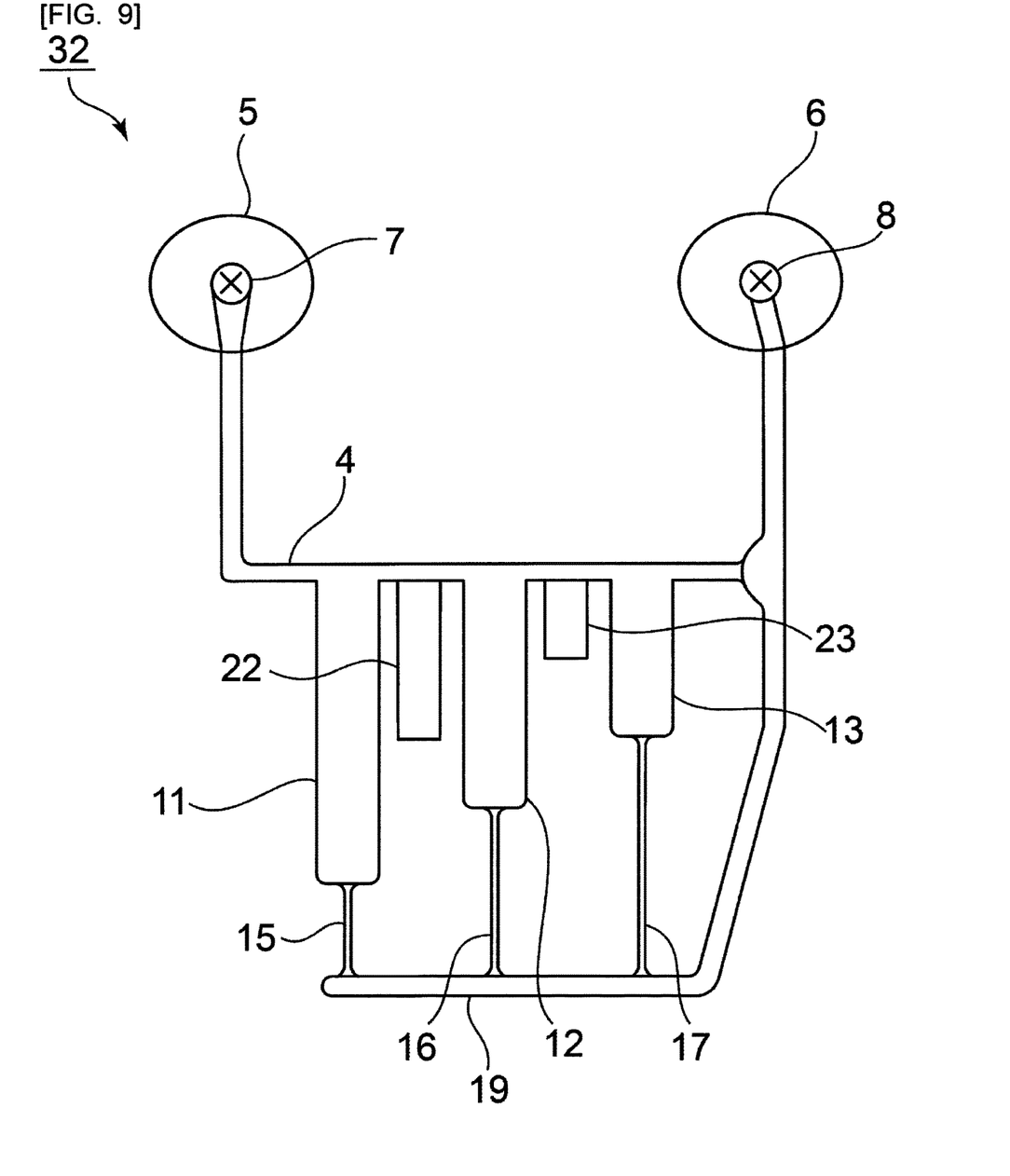
FIG. 9 is a schematic plan view for explaining a channel structure of a micro-fluid chip according to a sixth embodiment of the present invention.

A channel structure 31 of the micro-fluid chip of the fifth embodiment shown in FIG. 8 is arranged so that the length of the sub-branch channel 22>the length of the sub-branch channel 23. Further, a channel structure 32 of the micro-fluid chip of the sixth embodiment shown in FIG. 9 is arranged so that the length of the branch channel 11>the length of the branch channel 12>the length of the branch channel 13, and the length of the sub-branch channel 22>the length of the sub-branch channel 23. As shown in the channel structures 31,32, the lengths of the plurality of branch channels may be different from each other, and the lengths of the plurality of sub-branch channels may be different from each other.

Figure 10:
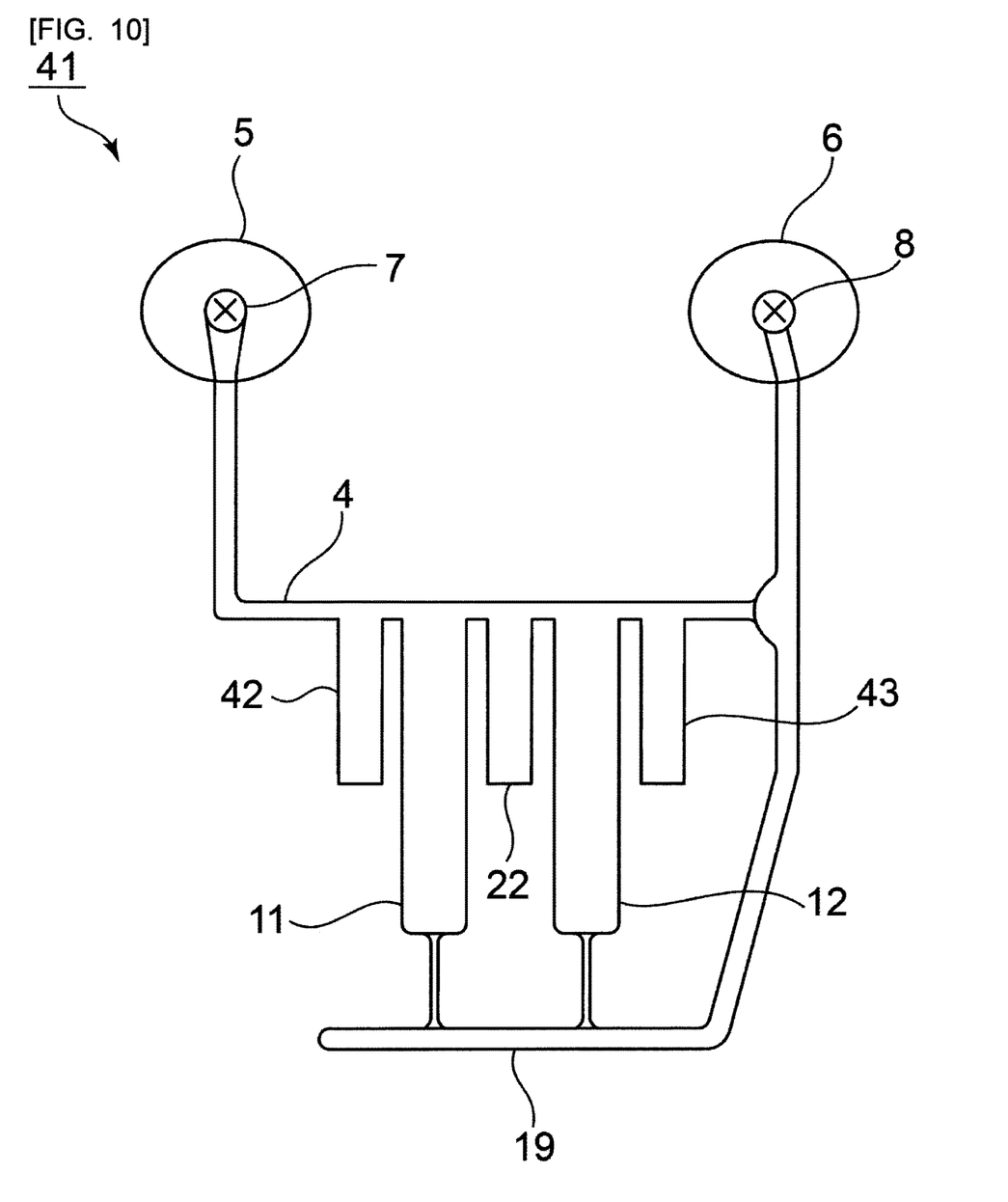
FIG. 10 is a schematic plan view for explaining a channel structure of a micro-fluid chip according to a seventh embodiment of the present invention.

Furthermore, as shown in a channel structure 41 of the micro-fluid chip of the seventh embodiment shown in FIG. 10, sub-branch channels 42, 43 may be provided on the upstream side or the downstream side of the main channel 4 relative to the portion where the plurality of branch channels 11, 12 are provided. That is, the sub-branch channel 42 or the sub-branch channel 43 may be provided at a portion other than the portion between the adjacent branch channels 11 and 12.

Figure 11:
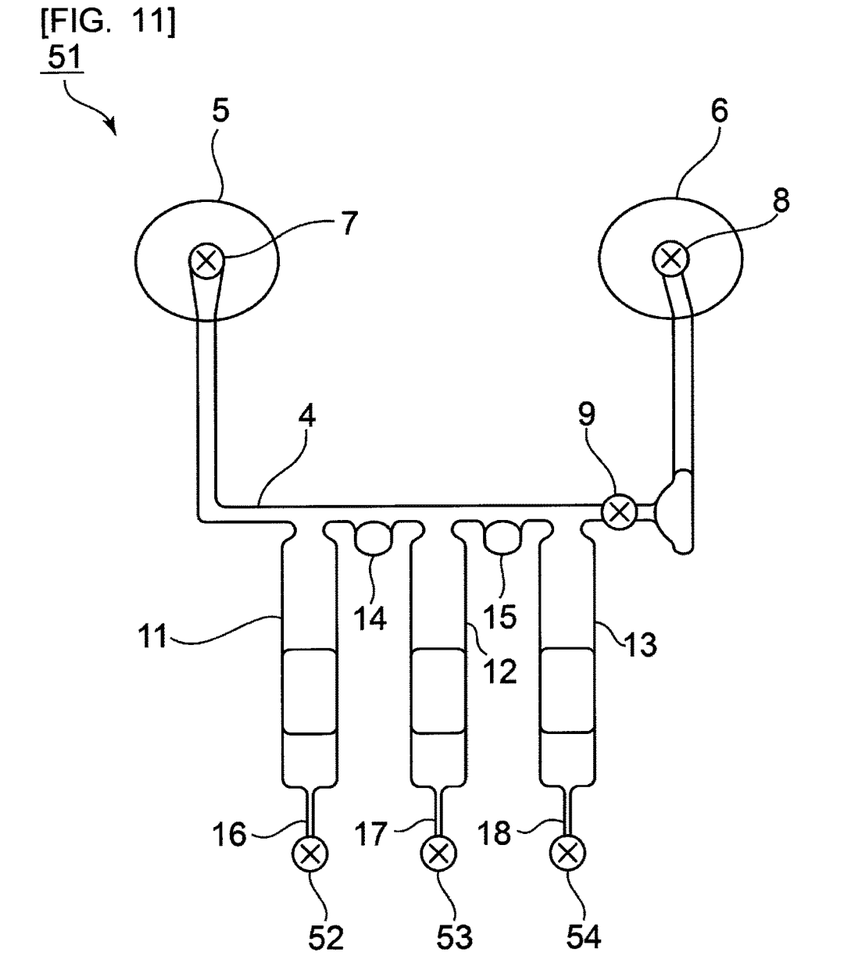
FIG. 11 is a schematic plan view for showing a channel structure of a micro-fluid chip according to an eighth embodiment of the present invention.

In FIG. 2, the connection channel 19 is provided, but, as in a channel structure 51 of the eighth embodiment shown in FIG. 11, valves 52 to 54 may be provided on the downstream side of the first to third branch channels 11 to 13 without providing the connection channel 19. That is, the fluid after the reaction may be discharged from another channel by opening the valves 52 to 54, without returning the fluid to the main channel 4.

Figure 12:
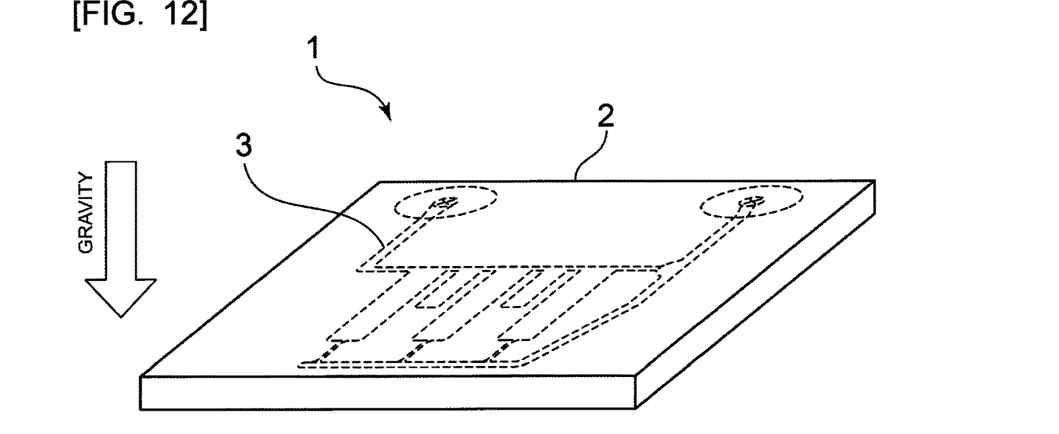
FIG. 12 is a perspective view showing a micro-fluid chip according to a ninth embodiment of the present invention.
Figure 13:
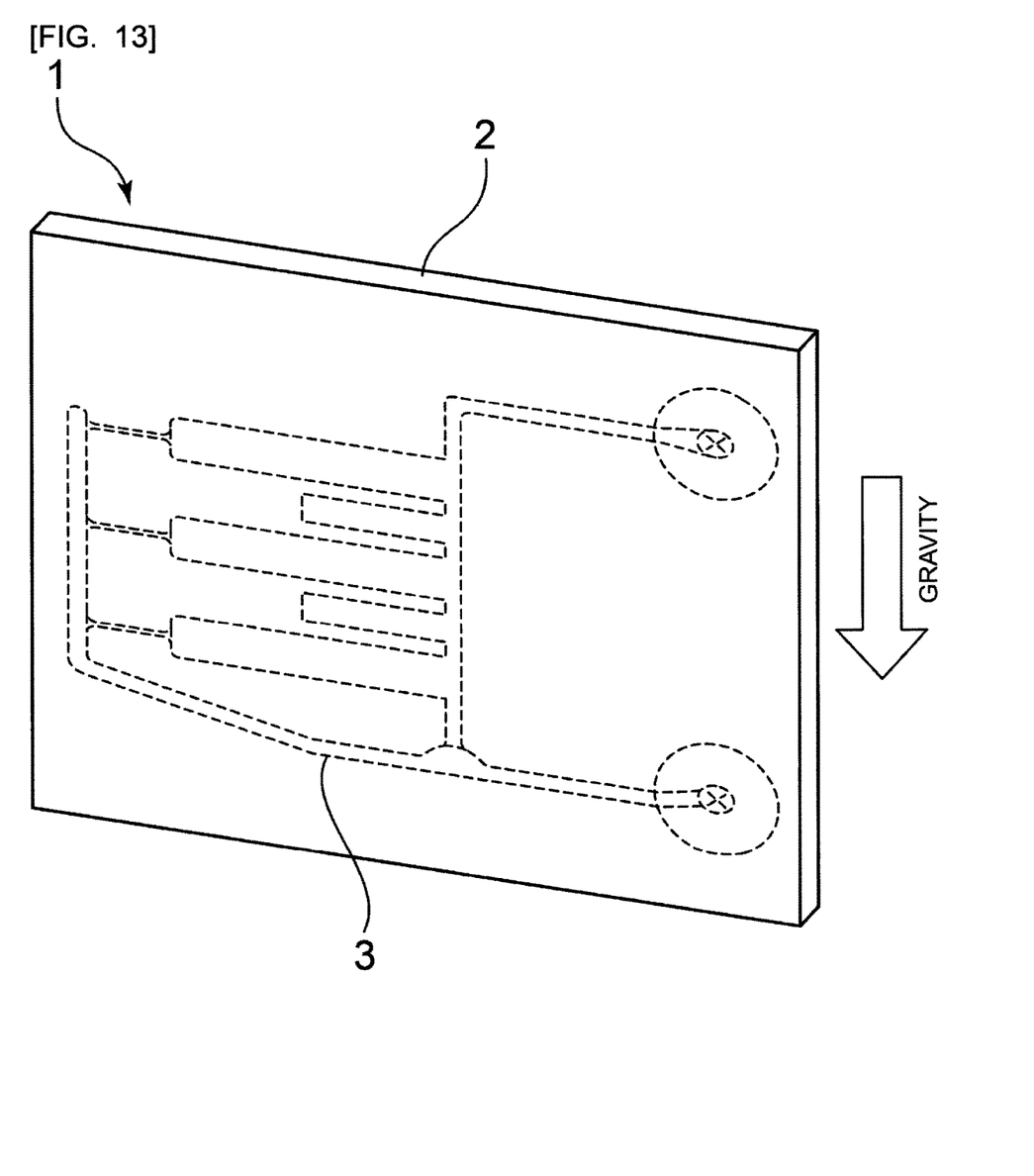
FIG. 13 is a perspective view for explaining a method of using the micro-fluid chip according to the ninth embodiment of the present invention in which a main channel is arranged in a vertical direction.

As in the ninth embodiment shown in FIG. 12, the micro-fluid chip 1 may be used by arranging a plane including the plurality of branch channels 11 to 13 in a direction orthogonal to the vertical direction, that is, in the direction shown in FIG. 12. Alternatively, as shown in FIG. 13, the micro-fluid chip 1 may be used by arranging the plane including the plurality of branch channels 11 to 13 in the vertical direction.

The fluid in the micro-fluid chip according to the present invention is not limited to specimens and reaction liquids for use in the PCR reaction, and can be widely used with various analysis methods involving heating of fluid.

REFERENCE SIGNS LIST

1 Micro-fluid chip
2 Chip main body
3 Channel structure
4 Main channel
4a-4d Inner walls
5 Inflow port
6 Outflow port
7-9 Valves
11-13 Branch channels
14, 15 Sub-branch channels
16-18 Channel resistance portions
19 Connection channel
21, 24, 27, 31, 32, 41, 51 Channel structures
22, 23, 25, 26, 28, 29, 42, 43 Sub-branch channels
52-54 Valves

The invention claimed is:

1. A micro-fluid chip having a channel structure through which a fluid is delivered, the channel structure comprising:
a main channel having an inflow port through which the fluid enters, and an outflow port through which the fluid flows out;
a plurality of branch channels connected to the main channel, each of the branch channels having an inflow end on a side connected to the main channel and an outflow end that is an end portion on an opposite side to the inflow end;
a sub-branch channel connected to the main channel between at least one pair of adjacent branch channels among the plurality of branch channels, the sub-branch channel having an inflow end on a side connected to the main channel, and the sub-branch channel having no outflow end; and
a connection channel connected to the outflow end side of the plurality of branch channels, wherein the connection channel is connected to the main channel.

2. The micro-fluid chip according to claim 1, wherein the inflow end of the sub-branch channel is open to an inner wall surface of the main channel shared by the inflow ends of two or more of the branch channels.

3. The micro-fluid chip according to claim 2, wherein an inner wall of the main channel where the branch channels and the sub-branch channel are open is an inner wall positioned in a direction orthogonal to a direction in which the branch channels extend.

4. The micro-fluid chip according to claim 3, wherein a transverse cross section of the main channel is rectangular.

5. The micro-fluid chip according to claim 1, wherein the sub-branch channel is provided at all positions between adjacent branch channels.

6. The micro-fluid chip according to claim 1, wherein an inflow end and an outflow end of the main channel are provided with a seal part capable of stopping the fluid from moving.

7. A micro-fluid chip having a channel structure through which a fluid is delivered, the channel structure comprising:
- a main channel having an inflow port through which the fluid enters, and an outflow port through which the fluid flows out;
- a plurality of branch channels connected to the main channel, each of the branch channels having an inflow end on a side connected to the main channel and an outflow end that is an end portion on an opposite side to the inflow end;
- a sub-branch channel connected to the main channel between at least one pair of adjacent branch channels among the plurality of branch channels, the sub-branch channel having an inflow end on a side connected to the main channel, and the sub-branch channel having a portion with a channel cross-sectional area larger than a channel cross-sectional area at the inflow end of the sub-branch channel connected to the main channel; and
- a connection channel connected to the outflow end side of the plurality of branch channels, wherein the connection channel is connected to the main channel.

* * * * *